United States Patent
Coleman et al.

(10) Patent No.: US 9,146,224 B2
(45) Date of Patent: Sep. 29, 2015

(54) LOW DEAD-VOLUME CORE-DEGASSING APPARATUS

(71) Applicant: Isotech Laboratories, Inc., Champaign, IL (US)

(72) Inventors: Dennis D. Coleman, Champaign, IL (US); Todd M. Coleman, Fairmont, IL (US)

(73) Assignee: Isotech Laboratories, Inc., Champaign, IL (US)

( * ) Notice: Subject to any disclaimer, the term of this patent is extended or adjusted under 35 U.S.C. 154(b) by 0 days.

(21) Appl. No.: 14/016,724

(22) Filed: Sep. 3, 2013

(65) Prior Publication Data

US 2014/0137635 A1    May 22, 2014

(51) Int. Cl.
*G01N 33/24*    (2006.01)
*G01N 1/22*    (2006.01)
*G01N 7/14*    (2006.01)

(52) U.S. Cl.
CPC ............ *G01N 33/241* (2013.01); *G01N 1/2294* (2013.01); *G01N 7/14* (2013.01); *G01N 33/24* (2013.01)

(58) Field of Classification Search
CPC ......... B65D 81/2023; G01N 1/22; G01N 7/14
USPC ........................................................ 73/864.63
See application file for complete search history.

(56) References Cited

U.S. PATENT DOCUMENTS

| | | | | |
|---|---|---|---|---|
| 4,951,496 | A * | 8/1990 | Aarts | 73/49.3 |
| 2004/0016672 | A1 * | 1/2004 | Savage et al. | 206/524.8 |
| 2004/0173034 | A1 * | 9/2004 | Srebro | 73/864.34 |

* cited by examiner

*Primary Examiner* — Hezron E Williams
*Assistant Examiner* — Mark A Shabman
(74) *Attorney, Agent, or Firm* — Patterson & Sheridan, LLP

(57) ABSTRACT

A canister for measuring the natural gas content of rock cores which (1) has an inner core-containment bag made of non-permeable plastic which can be flash evacuated, collapsing around the core and thus minimizing the amount of air present and improving the quality of the gas analyses and (2) which prevents the released gas from reacting with the outer canister. A procedure for using gas-sampling bags to periodically collect the gas released from the core so that (1) the volume of released gas can be measured at a later date using more convenient and precise laboratory methods, (2) the gas can be readily transported and stored, and (3) the gas can be easily submitted for analysis.

11 Claims, 2 Drawing Sheets

LOW DEAD-VOLUME CORE-DEGASSING APPARATUS

BACKGROUND OF THE INVENTION

1. Field of the Invention

Embodiments of the present invention relates to a canister for measuring the natural gas content of rock cores. Embodiments of the present invention also relates to a procedure for using gas-sampling bags to periodically collect the gas released from the core.

2. Description of the Related Art

Coals and shales have long been known to contain substantial quantities of natural gas, but the low permeability of these rocks has prevented this gas from being utilized. However, with newer technologies such as horizontal drilling and controlled rock fracturing, and with increasing gas prices, it is now economic to produce gas from many coals and shales that were previously of no interest. Although current technology makes it possible to produce this gas, this technology is very expensive and thus it is imperative that the drilling company has information on the gas content in the target rocks before undertaking a very expensive well-completion project.

The conventional method for determining the "in-situ" gas content of coals and shales is to collect core samples using traditional drilling techniques, sealing those cores into core degassing canisters, and measuring the quantity and quality of gas released over time. The rate of gas release is then used to estimate the amount of gas that was lost between the time when the core was cut, and when it was sealed into the canister. This is termed "lost gas". The total amount of recoverable in-situ gas in the rock is then assumed to be the sum of the lost gas and the released gas. Unfortunately, the amount of lost gas is sometimes a very significant fraction of the total and thus an accurate estimate of the lost gas is very important. Actually, those rocks which release their gas most readily are the ones of greatest economic interest, and the ones for which the accuracy of the lost gas volume is the most important, and the most difficult to estimate. The precision to which the lost gas can be estimated is very much dependant on the quality of data obtained by monitoring the degassing rate of the core samples in the canisters.

The canisters and procedures commonly used for core degassing studies are similar to those proposed by the US Bureau of Mines over 30 years ago. The typical degassing canister consists of a piece of aluminum pipe about 4" in diameter and from one to two feet long (although different sizes are available for different sized cores). One end of the pipe has an end cap welded on, and the other end has a flange welded on that will allow bolting on a top, which consists of an aluminum disk of the same diameter as the flange, and sealed with a rubber gasket or o-ring. Generally this top cap has ports through it that allow attaching a valve, a pressure gauge, and sometimes a thermocouple.

When a core is drilled, as soon as it is received at the surface and extruded from the core barrel, workers must cut it into appropriate lengths and then transfer sections of the core to empty degassing canisters. As quickly as possible, the canister is sealed by applying the lid and then inserting and tightening the bolts evenly. The time when the canister is sealed is recorded. The buildup of pressure in the canister is monitored by watching the pressure gauge and provides a rough estimate of the amount of gas released.

Beginning a few minutes after the core is first sealed, and continued periodically thereafter (sometimes for several weeks), the gas is bled out of the canister and measured. The gas volume is generally measured by water displacement. One method consists of passing the gas into a water-filled graduated cylinder that is inverted in a pan of water such that the gas displaces the water in the cylinder. The amount of water displaced is then recorded to determine the amount of gas released. Another method involves displacing the water in a calibrated gas burette. Both of these methods generally involve using water displacement, which is very difficult during cold or freezing weather. The accuracy of these methods is very dependent on the calibration of the measurement equipment used and the skill of the person doing the measurements.

Several problems exist with current core-degassing canisters. Being custom made from welded aluminum or stainless steel, they are relatively expensive and are quite heavy. Also, because the dead-space around the core sample is generally air, the first samples taken from the canister may contain mostly air. To accurately determine what is being released from the core, the analysis of the sample must be mathematically corrected for the air derived from the dead space. The typical procedure for doing this is to analyze the oxygen in the sample, assume that all of that oxygen came from air contamination, and knowing that the ratio of nitrogen to oxygen in air is quite constant at 3.73, and that the ratio of oxygen to argon in air is 22.4, subtract off the oxygen and an appropriate amount of nitrogen and argon to determine the chemical makeup of an "air free" sample. One problem with this is that coal, and minerals in the coal, are highly reducing and will react with oxygen. Therefore, using oxygen to estimate the amount of air can result in greatly underestimating the amount of air contamination, and over estimating the amount of nitrogen in the released gas, which decreases its heating value. Some have attempted to use argon to make this correction, but this requires special analytical equipment and procedures that most gas analysis laboratories do not have. Also, coal gas and shale gas can contain some argon which is assumed to be entirely from air, resulting in over-estimation of the amount of air contamination. Some have tried to fill the canister with water to displace the air, but this ads several other problems such as providing an environment conducive to bacterial degradation of both the core material and the gas.

Another problem commonly encountered with existing core degassing equipment is chemical interaction between the gas and the material from which the canister is constructed. For example, most coal gas and shale gas contains carbon dioxide and water. When these two combine, they form carbonic acid. Carbonic acid can react with aluminum or steel (even stainless steel) to form a metal carbonate and hydrogen gas. Hydrogen that comes from a chemical reaction within the canister is not readily distinguished from hydrogen that occurs naturally within the rock. In some cases, the amount of hydrogen caused by reaction with the canister can exceed the amount of natural gas released from the coal and has a very negative impact on the released gas determination. Furthermore, some gas analysis laboratories do not have the capability to accurately measure hydrogen and so it is just ignored.

SUMMARY OF THE INVENTION

The present invention uses a, non-permeable plastic, core-containment bag that begins accumulating the desorbed gas as soon as the bag is sealed, even before placing it into the canister. The bag is hermetically sealed using a standard heat sealer and thus, even if the outer canister leaks, the sample is not lost or contaminated. Using a standard vacuum-packing sealer, the core-containment bag can be flash evacuated, removing almost all of the air. The gas contacts only the core-containment bag and thus the type of material used for the outer canister is not critical, so long as it is leak free and can withstand the minor pressure buildup that occurs. This allows the use of less expensive materials for the canister and thus the canister may be constructed primarily of lightweight, inexpensive, and readily accessible PVC pipe and pipe fittings.

Because the core-containment bag is enclosed within the outer canister, the bag itself never experiences any pressure as the pressure outside the bag is always the same as that inside. Because the gas contacts only the core-containment bag and the top fitting, there is no aluminum or steel with which it can react to produce hydrogen. Because the air is removed almost immediately, by evacuation of the bag as it is sealed, oxidation of the core and the gases can not occur. Both the top and bottom are removable and can be used with bodies of different length. The ends are both attached with ring seals as opposed to flange seals which offer several advantages. The ring seal makes it faster and easier to make the seal reliably and quickly. Ring seals are relatively unaffected by pressure, compared to flange seals where the pressure forces the flange away from the sealing gasket. Because the lid does not need to be held down tightly against the gasket with bolts, the lid does not need to be of such heavy construction. The two piece rotating bottom makes it extremely quick to achieve a seal. The seal is made as soon as the bottom is in place, even before the bolts are tightened. The bottom can be made of clear plastic so that the contents can be seen.

Even if the canister leaks, the gas from the core is entirely contained within the interior bag, which is sized so that it would just expand against the sides of the canister and would not inflate and burst. If the canister is sealed, but the interior bag leaks, the gas from the core is still entrapped within the outer canister. Although contaminated with air, it is no worse off than with current methods, and reaction with the metal canister is still prevented. The pressure gauge on the top, which is in contact with only the air surrounding the interior bag, allows an estimate of the volume of gas in the container without actually contacting the gas. The self sealing valve on the cap allows using a standard tire pump to impose a slight pressure around the outside of the core-containment bag, so that it collapses around the core when the gas is drained off. The ball valve is connected to the interior core-containment bag via a simple and reliable o-ring seal.

The low internal-volume of the ball valve and the Luer-type fitting on the outlet allows transferring gas to a gas-sample bag, such as that manufactured by Calibrated Instruments, Inc. and fitted with a Luer-type valve, without significant air contamination, or loss of sample gas. The volume of gas in the gas-sample bag can be measured at a known temperature and the gas can be analyzed directly from the bag, improving the accuracy of the analysis and the released gas measurement. Because the volume of the gas can be measured at any later time, it is not necessary to do so at the drill site, when conditions are frequently adverse. Doing the measurement under pleasant conditions, probably in a laboratory, can improve the quality of the measurement.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

| Reference Numbers | |
|---|---|
| Body | 1 |
| First Body End | 2 |
| Second Body End | 3 |
| Body O Ring Seat | 4 |
| Body O Ring | 5 |
| Flange | 6 |
| Sealing Disk | 7 |
| Disk O Ring Seat | 8 |
| Disk O Ring | 8a |
| Base Disk | 9 |
| Feet | 9a |
| Screws | 9b |
| Nut | 9c |
| Cap | 10 |
| Set Screws | 10a |
| Cap Aperture | 10b |
| Chamber Valve | 11 |
| Pressure Gauge | 12 |
| Central Stem | 13 |
| Retaining Nut | 14 |
| Central Stem Flange | 15 |
| Central Stem Internal Gasket | 16 |
| Central Stem External Gasket | 16a |
| Containment Bag Valve | 17 |
| Removable Seal | 18 |
| Luer Fitting | 19 |
| Core Containment Bag | 20 |
| Core Containment Bag First End | 21 |
| Core Containment Bag Aperture | 22 |
| Core Containment Bag Second End | 23 |

Figure 1:
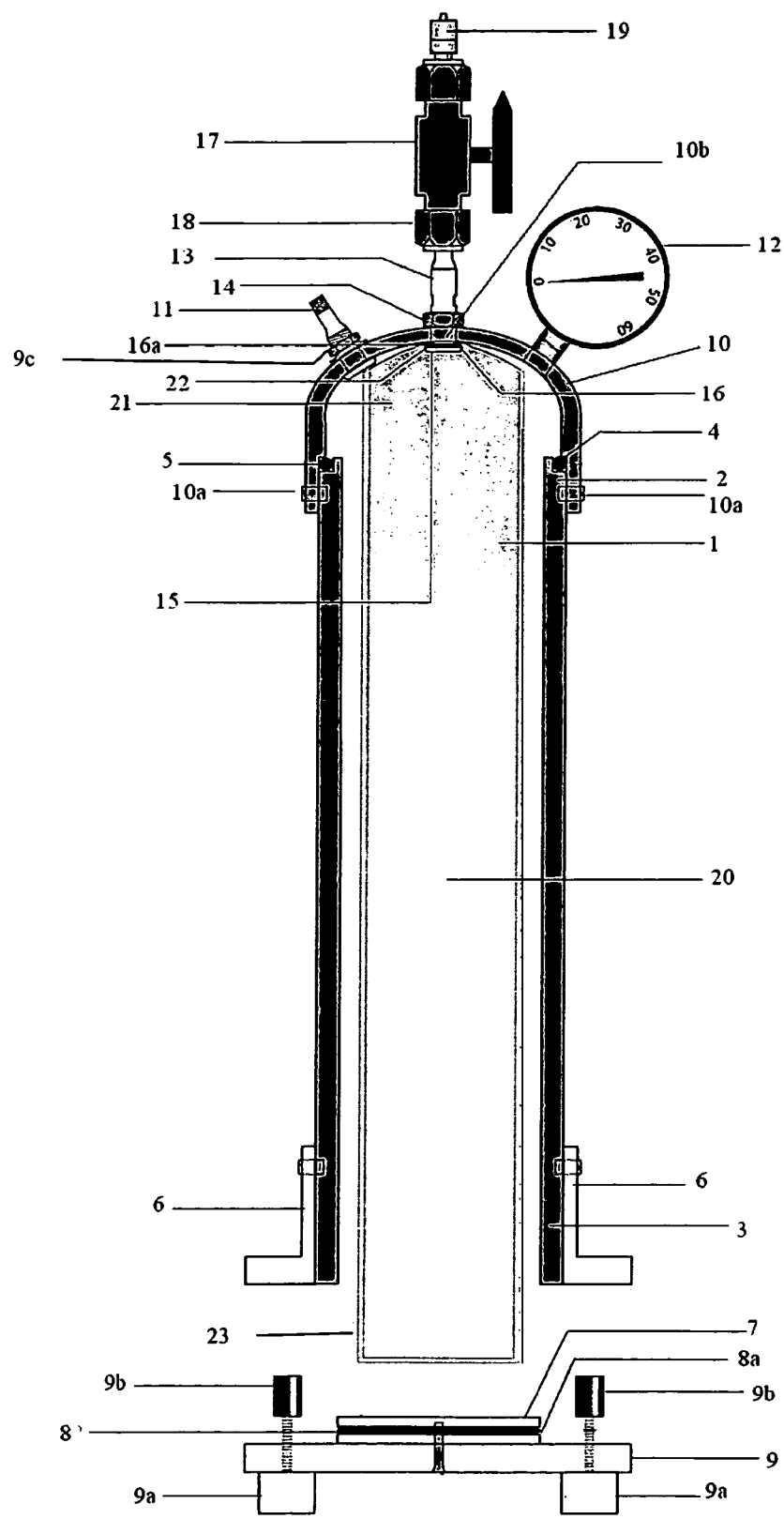
FIG. 1 is a side cross sectional view of the core degassing apparatus.
Figure 2:
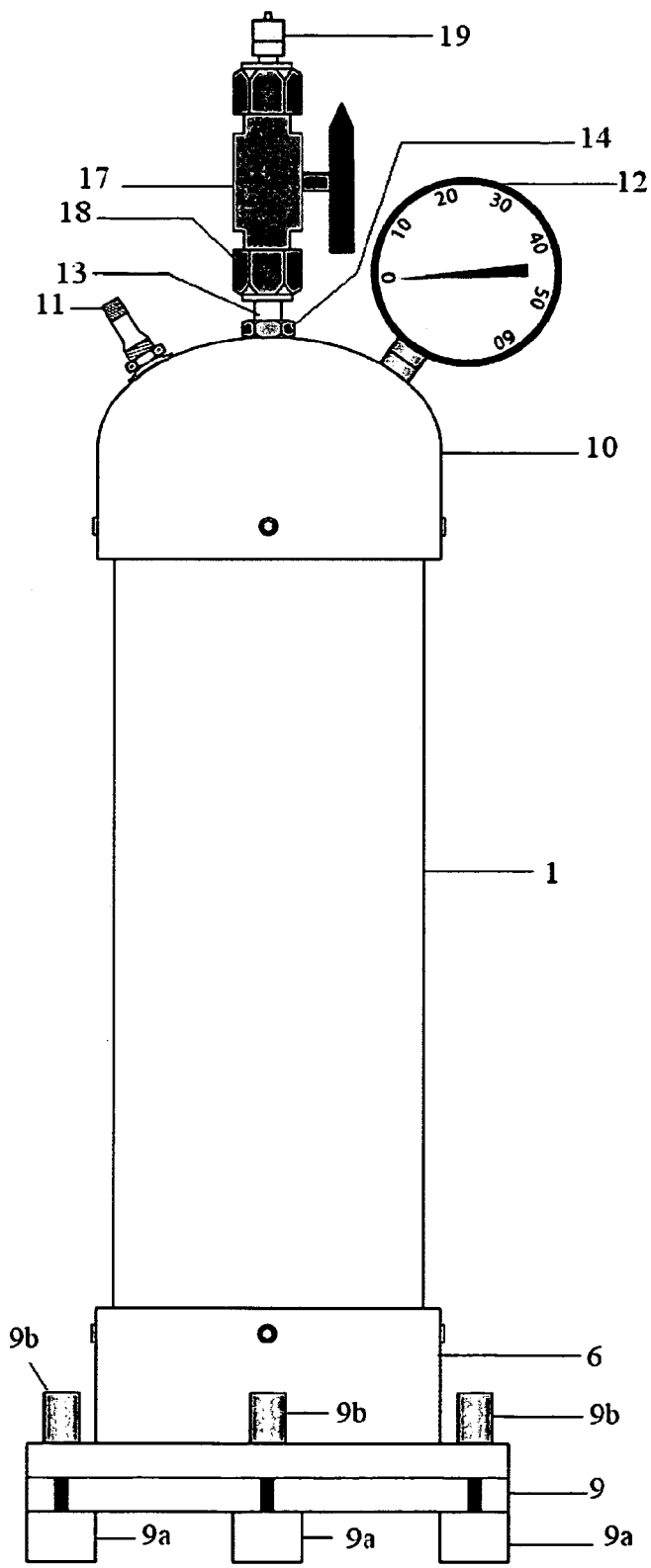
FIG. 2 is a side view of assembled apparatus.

FIG. 1 illustrates the four main components of the core degassing apparatus. Body 1 exhibits first body end 2 and second body end 3. First body end 2 exhibits body o-ring seat 4 which is machined from the tubular circumference of first body end 2 forming a lip upon which body o-ring 5 rests. Second body end 3 is inserted and fixed within circular flange 6. Sealing disk 7 is designed to be of such a diameter that it fits within second body end 3. Disk o-ring seat 8 is machined into the edge of sealing disk 7 and provides a recess where disk o-ring 8a is inserted into disk o-ring seat 8a. Sealing disk 7 may be inserted within second body end 3 creating an air tight seal for body 1. Sealing disk 7 is attached to base disk 9. Base disk 9 may exhibit a plurality of feet 9a as well as a plurality of screws 9b which are inserted through corresponding apertures in flange 6. A plurality of nuts 9c are then threaded over screws 9b thus securing base disk 9 and sealing disk 7 respectively over and within second body end 3.

Base disk 9 may be made of a transparent substance to allow a quick determination of whether the core degassing canister is loaded. Cap 10 is capable of being placed over first body end 2, with cap 10 making contact with and sealing against body o-ring 5. A plurality of set screws 10a may be inserted through cap 10 securing cap 10 to first body end 2. Cap 10 also exhibits chamber valve 11 and pressure gauge 12. Both chamber valve 11 and pressure gauge 12 are connected with the interior of body 1. When body 1 has sealing disk 7 and cap 10 in place, it thus creates an air tight container.

The core containment bag 20 exhibits a core containment bag first end 21 and a core containment bag second end 23.

Core containment bag second end 23 is open and is capable of receiving the core material and further capable of being vacuum sealed. Core containment bag first end 21 exhibits a core containment bag aperture 22. Central stem 13 is inserted through core containment bag aperture 22 then through Central stem internal gasket 16 then through cap aperture 10b. Central stem 13 is tubular in nature. Retaining nut 14 is then disposed over central stem 13 thereby holding the central stem 13 in place and sealing the core containment bag 20 to the central stem 13 thus allowing a fluid connection with the interior of core containment bag 20.

Preparation of the apparatus consists of inserting a new core containment bag 20 into the core degassing apparatus. Core containment bags of appropriate size can be made up in advance having a core containment bag aperture 22 in the core containment bag first end 21 to accept the central stem 13. After placing the Central stem internal gasket 16 on the central stem 13 to seal against the core containment bag 20, the central stem 13 is inserted through the core containment bag aperture 22 and then through central stem external gasket 16A, then through the cap aperture 10B and tightly secured with the nut 9C. The containment bag valve 17 is then attached to the central stem 13, secured, with a removable seal in the form of a compression fitting, and closed.

The open core containment bag second end 23 should protrude out the bottom of the degassing apparatus. A core sample can then be inserted into the core containment bag 20. The use of a temporary plastic sleeve wrapped around the core allows keeping the inside of the core containment bag 20 clean. Once the core is inserted completely into the core containment bag 20, the temporary plastic sleeve is removed and the core containment bag second end 23 is placed in a vacuum sealer (typically used for vacuum packing food) which quickly evacuates the air from the containment bag 20 surrounding the core and welds the core containment bag 20 shut. Another option is to evacuate the air from the sample containment bag 20 by connecting a vacuum pump to the core containment valve 17 after sealing the core containment bag 20.

Any portion of the core containment bag 20 which protrudes from the second body end 3 is pushed into the chamber and the sealing disk 7/base disk 9 assembly is then inserted into second body end 3. Screws 9b are then inserted into the corresponding apertures in the flange which presses sealing disk 7 with the disk o-ring into the bottom of the second body end 3.

The rate at which the core is releasing gas can be observed by monitoring the pressure build up on pressure gauge 12. Gas that is released from the core is contained within the core containment bag 20 and because of the flash evacuation that took place at the time of the core containment bag second end 23 was sealed, the amount of air contamination is minimal. As gas is released from the core, core containment bag 20 will compress and press against the air within body 1. Because body 1 is sealed, the pressure within the core containment bag 20 will achieve equilibrium and be eventually the same as the pressure surrounding it which is monitored by pressure gauge 12.

The first gas samples are generally collected a few minutes after sealing core containment bag second end 23 depending, however, on the degassing rate. To take a sample, all that must be done is to attach the Lure valve on an empty, evacuated gas sampling bag (not shown) to the Lure fitting 19 on the containment valve 17, here configured as a ball valve. The containment valve 17 is then opened. The gas which has accumulated within the core containment bag 20 will then be transferred into the empty gas sampling bag. At this point a pump in the form of a tire pump or bicycle pump can be attached to the chamber valve 11 and the space within body 1 surrounding core containment bag 20 can be slightly pressurized. This is slight pressure collapses the core containment bag 20 around the core and facilitates removal of virtually all the gas that has been released by the core but is not sufficient to stress the core containment bag 20. Pressurization of body 1 through chamber valve 11 need only be done once.

Once the sample has been transferred to the gas sampling bag, chamber valve 11 may be closed, the time recorded, and the gas sample bag can be removed. Although it will be necessary to measure the volume of gas in the gas sample bag, this can be done at a later time because the sample can be preserved for several months, if necessary in the gas sample bag.

An alternative procedure would be to attach a gas sampling bag to open containment valve 17 as soon as the sealing disk 7/base disk 9 assembly is sealed onto second body end 3. The chamber can be slightly pressurized at this time via chamber valve 11. Because the sample bag will expand as it collects the gas, the rate of degassing can be observed visually. Either at a predetermined time, or when the bag is full, containment valve 17 can be momentarily closed and the gas sample bag can be replaced with another empty gas sample bag. This procedure allows the core to degas under constant pressure which is of course is atmospheric pressure.

The gas collected in the gas-sample bag can me measured and analyzed at a convenient time and location, and need not be done at the drill site. To measure the volume of gas in the gas-sample bag, the gas can be drawn into a water filled gas burette attached to a leveling bulb. Once the gas is entirely drawn into the gas burette, the valve at the top of the burette can be closed and the leveling bulb raised until the water level in the burette is the same as that in the leveling bulb. The volume of gas can then be read from the calibrations on the burette. This method uses conventional equipment and is relatively easy, but has the disadvantage of possibly causing some slight contamination of the sample gas from equilibration with gas dissolved in the water in the gas burette, which could be air, or the previous sample.

A more efficient method is to measure the volume of gas in the gas-sample bag by water displacement. A pan of water can be weighed on a pan balance. If the gas-sample bag is then forced down into the water by a metal screen, the observed increase in weight on the pan balance is proportional to the volume of the gas. The buoyancy of an empty gas-sample bag must be measured and this value subtracted from the buoyancy of the sample filled gas-sample bag. With either method of volume measurement, the volumes must be corrected for temperature. The primary advantage of the buoyancy method is that it is quick and easy, and the integrity of the sample is entirely unaffected as the gas never contacts the water directly.

The chemical composition of the gas in a gas-sample bag may then be determined using conventional gas chromatography by inserting a septum plug into the Luer valve on the bag, and extracting gas with a syringe for analysis.

While the foregoing is directed to embodiments of the present invention, other and further embodiments of the invention may be devised without departing from the basic scope thereof, and the scope thereof is determined by the claims that follow.

The invention claimed is:
1. A core degassing apparatus for degassing a core sample, comprising:
a body including a chamber having an open end;

a sealing disk releasably coupled to the body and configured to close the open end of the chamber;

a core containment bag disposed within the chamber, wherein the core containment bag includes an open end for receiving the core sample and an aperture for communicating fluid from the core sample and wherein the core containment bag is sealable after receiving the core sample.

2. The core degassing apparatus of claim 1, further comprising a central stem fluidly connected to the core containment bag.

3. The core degassing apparatus of claim 1, further comprising a valve fluidly connected to the chamber.

4. The core degassing apparatus of claim 1, further comprising a pressure gauge fluidly connected to the chamber.

5. The core degassing apparatus of claim 1, further comprising a cap sealably and releasably connected to the body.

6. The core degassing apparatus of claim 5, wherein at least one of a valve, a pressure gauge, and a central stem are sealably disposed through the cap.

7. The core degassing apparatus of claim 6, wherein at least one of the cap, the body, and the sealing disk are composed of clear plastic.

8. The core degassing apparatus of claim 1, wherein the core containment bag comprises a non-permeable material, whereby a gas of the core sample may be retained.

9. The core degassing apparatus of claim 1, wherein the containment bag is expandable.

10. The core degassing apparatus of claim 9, wherein expansion of the containment bag is limited by the body.

11. The core degassing apparatus of claim 1, wherein the containment bag is flexible.

\* \* \* \* \*

UNITED STATES PATENT AND TRADEMARK OFFICE
CERTIFICATE OF CORRECTION

Page 1 of 1

PATENT NO. : 9,146,224 B2
APPLICATION NO. : 14/016724
DATED : September 29, 2015
INVENTOR(S) : Coleman et al.

It is certified that error appears in the above-identified patent and that said Letters Patent is hereby corrected as shown below:

Title Page, Related U.S. Application Data:

Please insert

--(63) Continuation of application No. 12/386,368, filed on Apr. 17, 2009, now Pat. No. 8,522,599.

(60) Provisional application No. 61/124,597, filed on Apr. 17, 2008.--.

Signed and Sealed this
Seventh Day of June, 2016

Michelle K. Lee
*Director of the United States Patent and Trademark Office*